United States Patent [19]

Bisagni et al.

[11] Patent Number: 4,870,180
[45] Date of Patent: Sep. 26, 1989

[54] 1,2-DIHYDRO-4-METHYL-1-OXO-5H-PYRIDO(4,3-B)INDOLES AND THE PROCESS FOR THEIR SYNTHESIS

[75] Inventors: Emile R. Bisagni, Orsay; Hung C. Nguyen, Les Ulis; Paul M. de Cointet, Toulouse, all of France

[73] Assignee: Sanofi and Centre National De La Recherche Scientifique, Paris, France

[21] Appl. No.: 26,574

[22] Filed: Mar. 17, 1987

[30] Foreign Application Priority Data

Mar. 17, 1986 [FR] France ................................ 86 04201
Oct. 24, 1986 [FR] France ................................ 86 15290

[51] Int. Cl.⁴ .......................................... C07D 471/04
[52] U.S. Cl. ..................................................... 546/86
[58] Field of Search ............................................ 546/86

[56] References Cited

U.S. PATENT DOCUMENTS 2,866,788 12/1958 Pachter ................................. 548/86

FOREIGN PATENT DOCUMENTS 1082598 2/1956 Fed. Rep. of Germany ........ 546/86

OTHER PUBLICATIONS

Abramovitch et al., *J. Chem. Soc.*, 1956, pp. 4589–4592.
Phillips, *Organic Reactions*, vol. 10, chapter 2, pp. 144–177.
Robinson, *The Fischer Indole Synthesis*, 1982, pp. 28–59.
Lee et al. *Heterocycles*, vol. 16, No. 7, Jul. 1981, pp. 1081–1084.

*Primary Examiner*—Mary C. Lee
*Assistant Examiner*—Linda Nothington
*Attorney, Agent, or Firm*—Wegner & Bretschneider

[57] ABSTRACT

The present invention relates to new compounds which are the 1,2-dihydro-4-methyl-1-oxo-5H-pyrido(4,3-b)indoles with the formula (I):

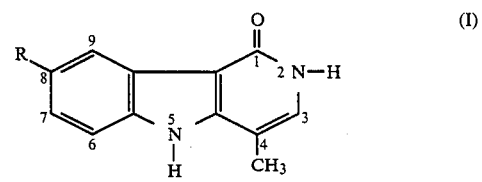

in which R represents hydrogen or an alkoxy or aryl carbonyloxy group. These compounds are intermediates of synthesis in the preparation of compounds which can be used in the pharmaceutical industry. The invention is also concerned with their synthesis.

7 Claims, No Drawings

1,2-DIHYDRO-4-METHYL-1-OXO-5H-PYRIDO(4,3-B)INDOLES AND THE PROCESS FOR THEIR SYNTHESIS

The invention relates to new compounds which are 1,2-dihydro-4-methyl-1-oxo-5H-pyrido(4,3-b)indoles with the following formula:

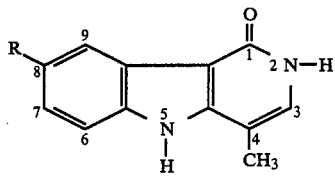

in which R represents hydrogen or a $C_1$-$C_4$ alkoxy group, linear or branched, or a $C_6$-$C_{10}$ aryl carbonyloxy group. These derivatives are intermediates in the preparation of compounds with the formula (A):

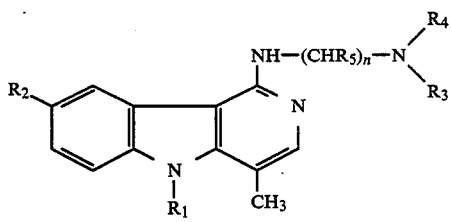

in which n represents an integer from 2 to 4, $R_1$ represents hydrogen or a $C_1$-$C_4$ alkyl group, $R_2$ represents hydrogen or a hydroxy group or a $C_1$-$C_4$ alkoxy group, $R_3$ and $R_4$, independently of each other, are hydrogen, a $C_1$-$C_4$ alkyl group or a hydroxyalkyl group, $R_5$ can be identical or different, and represents hydrogen, a $C_1$-$C_4$ alkyl group or a hydroxy group. These compounds (A), which are endowed with useful anti-tumour properties, are the subject of the application Ser. No. 042,896, U.S. Pat. No. 4,835,160 filed this same day by the applicants and claim the priority of the French patent application No. 86,04,202 dated the 17th Mar. 1986.

The 1,2-dihydro-1-oxo-5H-pyrido(4,3-b)indole and certain of its derivatives have been previously described in the literature, notably by CH. S. LEE et al. (Heterocycles, 16, 1081–1084, (1981)) and by C. DUCROCQ et al. (J. Heterocycl. Chem., 12, 963–967, (1975)).

But these derivatives, the synthesis of which is different from the process which is the subject of the invention, do not include either the methyl groups in position 4 nor a substituent in position 8, so that they cannot be used as intermediates in the preparation of the compounds with the formula (A).

Furthermore, the method of preparation of the compounds with the formula (I) used in the parallel patent application Ser. No. 042,896 filed this same day is that described by E. BISAGNI et al. (Synthesis, 1984, 765). This method is characterized in that a para-alkyloxy-phenylhydrazine in great excess reacts on the 1,2-dihydro-4-hydroxy-5-methyl-2-oxopyridine at high temperature in order to lead to the compounds with the formula (I). But whatever the operational conditions employed, the yield in 8-alkoxy-1,2-dihydro-4-methyl-2-oxo-5H-pyrido(4,3-b)indole (I) always remains below 20% as referred to oxopyridine. Now, the new preparation process, which is the subject of the invention, enables access to the compounds with the formula (I) with a yield greater than 50% referred to oxopyridine. This new process is characterized in that;

(1) by reaction of the 1,2-dihydro-4-hydrazino-5-methyl-2-oxopyridine (prepared according to the method described by E. BISAGNI, French patent application No. 85,08,871 of Mar. 22nd 1985, with a yield of 76% referred to 1,2-dihydro-4-hydroxy-5-methyl-2-oxopyridine), on cyclohexanone possibly carrying the substituent R in position 2, hydrazone is obtained with the formula (II):

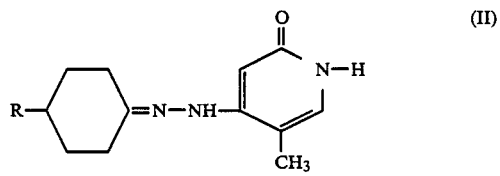

in which R has the same significance as in formula (I).

(2) hydrazone with the formula (II) is cyclized according to FISHER'S reaction to form the 1,2,6,7,8,9-hexahydro-4-methyl-1-oxo-5H-pyrido(4,3-b)indole with the formula (III)

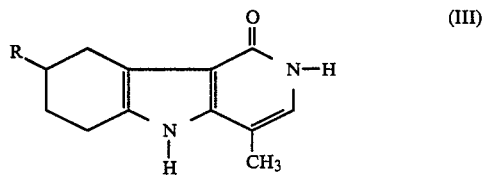

The hexahydropyrido indole with the formula (III) is dehydrogenated by the action of palladized charcoal in order to form the 1,2-dehydro-4-methyl-1-oxo-5H-pyrido(4,3-b)indole with the formula (I).

The formation of the hydrazone (II) is carried out at the temperature of reflux of a polar solvent such as ethanol.

The cyclization of the hydrazone (II) is obtained by heating at temperatures between 200° C. and 280° C. at reflux of an inert solvent, such as diphenyl ether, in the absence of the catalyst.

The aromatization of the compound with the formula (III) which leads to the 1-oxo-pyrido indole of formula (I) takes place in the same solvent as that used in the preceding stage, at high temperature and in the presence of a catalyst such as palladized charcoal, in such a way that the intermediate isolation of the compound (III) is not indispensable.

Certain compounds with the formula (I) can also be prepared as follows:

(1.) By reaction of 4-hydrazone-5-methyl-2-oxo-1,2-pyridine, prepared according to the method described by E. BISAGNI (French patent application No. 85.04.871 dated 22nd Mar. 1985), on 3,3-dimethyl-1,5-dioxa-spiro[3,5]undecanone or any other monoacetal of 1,4-cyclohexanedione prepared, for example, according to the method of J. M. KAMENKA [Bull. Soc. Chim. France, 3,4 87–88, 1983] there is obtained the hydrazone with the formula:

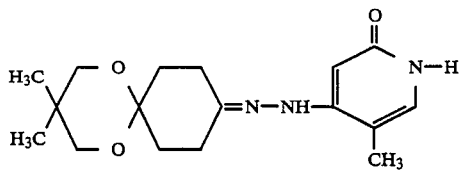

(2.) The hydrazone of formula (IV) is cyclized according to the FISHER reaction, and the cyclic derivative obtained is hydrolyzed to form the 4-methyl-6,7,8,9-tetrahydro-2H,5H-pyrido[4,3-b]indole-1,8-dione with the formula:

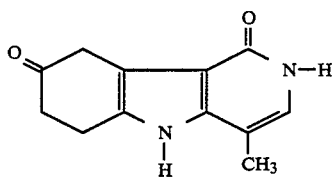

(3.) The pyrido-indoledione of formula (V) is dehydrogenated by the action of palladized charcoal in order to form 8-hydroxy-4-methyl-2H-pyrido[4,3-b]-1-indolone with the formula:

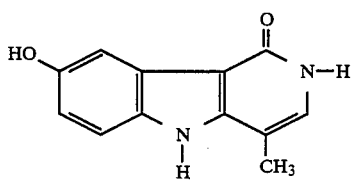

(4.) The hydroxyl derivative (VI) is esterified by action of an anhydride of an aromatic acid in order to form an 8-arylcarbonyloxy-4-methyl-2H,5H-pyrido[4,3-b]-1-indolone with the formula (I) in which $R_2$ represents the ($C_6$-$C_{10}$) aryl carbonyloxy:

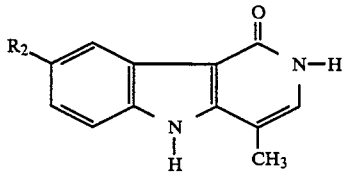

The formation of the hydrazone with the formula (IV) takes place at the reflux temperature of a polar solvent such as ethanol.

The cyclization of the compound with the formula (IV) is obtained by heating at temperatures between 200° C. and 280° C. at reflux of an inert solvent such as diphenyl ether.

After hydrolysis by a normal aqueous solution of hydrochloric acid taken to reflux, the aromatization of the compound with the formula (V), which leads to the compound with the formula (VI), takes place in the same solvent as that used in the preceding stage, at high temperature and in the presence of a catalyst such as palladized charcoal.

The esterification of the compound with the formula (VI) is carried out at the reflux temperature of a basic aprotic solvent such as pyridine.

The following examples are given by way of illustration of the present invention:

EXAMPLE 1

Preparation of 1,2-dihydro-8-methoxy-4-methyl-1-oxo-5H-pyrido(4,3-b)indole (formula (I) compound with R=OCH$_3$)

(A)

4-methoxy-1-[(1,2-dihydro-3-methyl-2-oxo-4-pyridyl)-hydrazono]cyclohexane (formula (II) compound with R=—OCH$_3$)

Into 500 ml of absolute ethanol, there is introduced 25 g (0.18 mole) of 1,2-dihydro-4-hydrazino-5-methyl-2-oxo-pyridine, then 25 g (0.195 mole) of 4-methoxy-cyclohexanone, which has been prepared according to the method of J. W. COOK et al. (J. Chem. Soc. 322–324, 1944). The medium is taken to reflux and after having passed through a homogeneous phase, it becomes heterogeneous because the expected hydrazone (II) precipitates progressively. After 4 hours of reflux, 250 ml of ethanol is eliminated by distilling at normal pressure. The medium is then cooled to 0° C. The precipitate formed is filtered off, washed with ethyl ether and dried. 38.8 g of hydrozone (II) is obtained.

Yield: 86%: m.p.: 270° C.

Calculated for $C_{13}H_{19}N_3O_2$: C, 62.68: H, 7.69: N, 16.87. Found: C, 62.79: H, 7.84: N, 16.84.

(B)

1,2,6,7,8,9-hexahydro-8-methoxy-4-methyl-1-oxo-5H-pyrido(4,3-b)indole (formula (III) compound with R=0CH$_3$)

Under agitation and under an atmosphere of nitrogen, 450 ml of diphenylether is taken to 80° C., then 20 g (0.08 mole) of the preceding hydrazone is added, and the medium is heated to reflux which is maintained for 30 minutes. After cooling to 50° C., 400 ml of toluene is introduced into the medium which is then cooled to 15° C. The precipitate formed is filtered off, washed with acetone, then with ethyl ether. In this way, 17.7 g of the expected hexahydropyridoindole is isolated. Yield: 95%, m.p. >270° C.

Calculated for $C_{13}H_{16}N_2O_2$: C, 67.22: H, 6.94: N, 12.06. Found: C, 67.12: H, 6.95: N, 12.16.

NMR 1H (CD$_5$N): δ: 1.85–2.07 (m, 2H, CH2-7): 2.21 (s, 3H, CH3-4); 2.66–2.94 (m, 2H, CH2-6): 3.35 (s, 3H, O-CH3); 3.57–3.93 (m, 3H, H-8+CH2-9): 6.94 (s, 1H, H-3); 11.54 (s, 1H, NH-2); 11.94 (s, 1H, NH-5).

(C)

1,2-dihydro-8-methoxy-4-methyl-1-oxo-5H-pyrido(4,3-b)indole 30 g of palladized carbon is introduced into 2 liters of diphenylether. Then, under agitation and under an atmosphere of nitrogen, the medium is taken to reflux temperature. Then, progressively, 134 g (0.58 mole) of hexahydropyrido-indole obtained according to stage B, is added and the medium is kept at reflux for about 1 hour after this addition until the end of the evolution of hydrogen. After having cooled to 50° C., 1 liter of toluene is introduced and the medium is cooled to 15° C. The precipitate formed is filtered off, then recrystallized from 1.5 liter of acetic acid. The pure product so obtained is filtered off, washed with acetone and then with ethyl ether. 97 g of the expected pure 1-oxo-pyridoindole is isolated. The acetic acid solution is concentrated under reduced pressure. The precipitate formed is filtered off, washed with acetone and then with ethyl ether. In this way again 15.6 g of the expected pure 1-oxo-pyridoindole is isolated.

Yield; 86%: m.p. >270° C.

Calculated for $C_{13}H_{12}N_2O_2$: C, 68.45: H, 5.30: N, 12.28. Found: C, 68.26: H, 5.15: N, 12.27.

NMR 1H [(CD$_3$)2SO]: δ: 2.26 (s, 3H, CH3-4); 3.84 (s, 3H, OCH3); 6.94 (q, 1H, H-7, J 7-6=8.6 Hz, J 7-9=2.8 Hz): 7.07 (s, 1H, H-3); 7.43 (d, 1H, H-6); 7.65 (d, 1H, H-9); 10.82 (s, 1H, NH-5); 11.55 (s, 1H, NH-2).

EXAMPLE 2

Preparation of 1,2-dihydro-8-methoxy-5-methyl-1-oxo-5H-pyrido(4,3-b)indole (compound of formula (I) with R=—OCH$_3$) without isolating the formula (III) compound Into 200 ml of diphenyl ether, 8.1 g (0.058 mole) of hydrazone, prepared according to the method described in stage A of example 1, is introduced. Then, under agitation and under an atmosphere of nitrogen, the medium is taken to reflux, which is maintained for 30 minutes. After cooling towards 100° C., there is then added, under an atmosphere of nitrogen, a suspension of 2 g of palladized charcoal at 10% in 30 ml of diphenyl ether. The medium is then heated to reflux for 30 minutes. After cooling to 60° C., 400 ml of ethanol is introduced and the medium is heated to reflux.

The palladized charcoal is filtered off hot, then washed with 100 ml of boiling ethanol.

This ethanol filtrate is added to the diphenylether-ethanol medium which is then concentrated under reduced pressure in order to eliminate the ethanol. 200 ml of toluene is added to the diphenylether phase. The precipitate obtained is filtered off, then recrystallized from ethanol. In this way, the 5.9 g of the expected 1-oxopyrido-indole is obtained.

Yield: 79.7% m.p. >270° C.

The product obtained has the same characteristics (IR; MNR) as the sample prepared according to the method No. 1 of example 1.

By way of illustration, there is described below the preparation of a compound with the formula (A), starting from a compound with the formula (I):

Preparation of (3-diethylamino-1-propylamino)-4,5-dimethyl-8-methoxy-5H-pyrido(4,3-b)indole (formula (A) compound with $R_1$=—CH$_3$, $R_2$=—OCH$_3$, $R_3$=$R_4$=—$C_2H_4$, $R_5$=H and n=3)

(A)

1-chloro-4-methyl-8-methoxy-5H-pyrido(4,3-b)indole 7 g of 1,2-dihydro-8-methoxy-4-methyl-1-oxo-5H-pyrido(4,3-b)indole is heated in 200 ml of phosphorus oxychloride at reflux for 3 days and the excess of oxychloride is evaporated off under reduced pressure. The residue is taken up in 100 ml of boiling water, the mixture is heated to boiling point for 3 minutes and filtered. The filtrate is alkalized cold with ammonia and the precipitate formed is separated, dried, then recrystallized from acetonitrile, giving 5.8 g of yellow microcrystalls.

Yield; 76%; m.p. 243°-245° C.

Calculated, for $C_{13}H_{11}ClN_2O$: C, 63.29: H, 4.49; N, 11.35; Cl, 14.37. Found: C, 63.02; H, 4.38; N, 11.28; Cl, 14.55.

NMR H1 [(CD3)2SO]; δ; 2.52 (d, 3H, CH3-4, JCH3-H-3=1 Hz); 3.91 (s, 3H, OCH3): 7.23 (q, 1H, H-7, J 7-6=9 Hz, J7-9=2.5 Hz): 7.60 (d, 1H, H-6); 7.87 (d, 1H, h-9); 8.04 (d, 1H, H-3).

(B)

1-chloro-4,5-dimethyl-8-methoxy-5H-pyrido(4,3-b)indole 20 g of 1-chloro-8-methoxy-4-methyl-5H-pyrido(3,2-b)indole (0.08 mole) is dissolved in 300 ml of anhydrous N,N-dimethylformamide, then 86 g of potassium carbonate (0.6 mole) is introduced and also 25 g of methyl iodide (0.178 mole) at 20° C. under agitation maintained for 24 hours.

The precipitate is filtered off. Then the solution is concentrated under reduced pressure. The second precipitate is filtered off. The two precipitates are then dissolved in boiling water acidified by an N aqueous solution of hydrochloric acid. The cooled aqueous solution is then neutralized with a dilute ammonia solution. The precipitate obtained is filtered off, washed with water, dried, and re-crystallized from ethanol. 15 g of the expected product is obtained.

Yield; 71%; m.p. 180° C.

Calculated for $C_{16}H_{13}ClNO_2$: C, 64.49: H, 5.03: N, 10.74: Cl, 13.60. Found: C, 64.73: H, 5.01: N, 10.52: Cl, 13.32.

NMR H1 [(CD3)2SO)]; δ; 2.28 (d, 3H, CH3-4, J CH3-H-3=1 Hz); 3.91 (s, 3H, OCH3); 4.14 (s, 3H, NCH3); 7.29 (q, 1H, 8-7, J 7-6=8.9 Hz, J 7-9=2.5 Hz); 7.70 (d, 1-H, H-6); 7.91 (d, 1N, H-9); 8 (d, 1H, H3).

(C)

1-(3-diethylamino-propylamino)-4,5-dimethyl-8-methoxy-5H-pyrido-(4,3-b)indole

This compound is prepared by the action of 1-chloro-4,5-dimethyl-8-methoxy-5H-pyrido(4,3-b)indole (1 g) on 3-diethylaminopropylamine (20 ml), taken to reflux for 44 hours. Then the excess of amine is distilled off under reduced pressure. The residue is taken up in 20 ml of water, alkalized with a normal aqueous solution of sodium hydroxide and finally extracted with methylene chloride. The organic phase is dried, then concentrated under reduced pressure. The crude product so obtained is purified by chromatography on an alumina column, eluting first with methylene chloride and then with a mixture of methylene chloride and methanol (98/2).

Yield: 85%; m.p. 107°-109° C.

NMR H1 [CD3)2SO]: δ: 0.99 (t, 2×3H, CH3-CH2): 1.81 (m, 2H, CH2-B); 2.50-2.54 (m, 3×2H, (CH2-CH3)+CH2—); 2.62 (d, 3H, CH3-4), J CH3-H-3=0.7 Hz); 3.60 (m, 2H, CH2—); 3.90 (s, 3H, OCH3); 4.05 (s, 3H, NCH3); 6.35 (t, 1H, NH); 7.09 (q, 1H, H-7, J 7-6=9 Hz, J 7-9=2.3 Hz); 7.52 (d, 1H, H-6); 7.69 (d, 1H, H-3); 7.74 (d, 1H, H-9).

EXAMPLE 3

Preparation of the 8-benzoyloxy-4-methyl-5H-pyrido(4,3-b)indole (formula) (I) compound in which R=$C_6H_5$—CO—O)

(A)

3,3-dimethyl-1,5-dioxa-9-[(5-methyl-2-oxo-1,2-dihydro-1H-4-pyridyl)-hydrazono]-spiro[5,5]undecane A mixture formed by 4-hydroxy-5-methyl-1H-2-pyridone (16 g), monoethyl ether of ethylene glycol (400 ml) and hydrazine hydrate (140 ml) is heated to reflux for 4 hours and evaporated to dryness under reduced pressure. The solid residue is taken up in 500 ml of boiling absolute ethanol, then filtered, and the filtrate is concentrated to one half.

After one night at ambient temperature, the crystallized solid is separated and dried. Colourless crystals (13 g) are obtained, corresponding to the hydrate of the compound sought, m.p.=135°–155° C.

Calculated for $C_6H_9N_3O,H_2O$: C, 45.85: H, 7.05: N, 26.74. Found: C, 45.29: H, 6.97: N, 26.03.

The mother liquors concentrated to 100 ml and left for one night at ambient temperature provided a new quantity of the compound (2.4 g). The total yield thus rises to 15.4 g, or 76%.

A mixture of 4-hydrazine-5-methyl-1H-2-pyridone (3.59 g) and of 3,3-dimethyl-1,5-dioxa-spiro[5,5]-9-decanone (7.92 g) in absolute ethanol (200 ml) is heated to reflux for 2 hours 15 minutes, then cooled to ambient temperature. The filtered solid is washed with ethanol, yielding 9 g of pure hydrazone. Evaporation of mother liquors leaves a solid residue which is taken up in 100 ml of boiling dioxane, cooled to the ambient, filtered, then recrystallized from ethanol, giving 1.2 g of the expected product. Yield: 90.3%: m.p. 260° C.

Calculated for $C_{17}H_{25}N_3O_3$: C, 63.92: H, 7.89: N, 13.16. Found: C, 63.64: H, 7.66: N, 12.84.

(B)

6,7,8,9-tetrahydro-4-methyl-2H,5H-pyrido(4,3-b)-1,8-indoledione

A mixture formed by the preceding hydrazone (2.3 g) in diphenylether (45 ml) is heated to reflux under an argon atmosphere for 40 minutes and allowed to cool to ambient temperature.

After the addition of 150 ml of xylene, the precipitate formed is separated and washed with xylene to give 2 g of crude intermediate, which is then hydrolyzed by heating to boiling point for 25 minutes in 100 ml of N hydrochloric acid, cooled and alkalized by the addition of potassium carbonate. The solid obtained is filtered off, dried and recrystallized from the minimum of ethanol to give 1.1 g of colourless micro-crystals corresponding to the hydrate of the expected indoledione.

Yield: 70.6%: m.p. >260° C.

Calculated for $C_{12}H_{12}N_2O_2$: C, 62.53: H, 5.98: N, 11.96. Found: C, 61.15: H, 5.97: N, 11.73.

NMR $H_1$ [$(CD_3)_2SO$]: δ: 2.15 (s, 3H, $CH_3$-4), 2.68 (t, 2H, $CH_2$-7), 3.06 (t, 2H, $CH_2$-6), 3.61 (s, 2H, $CH_2$-9), 6.71 (s, wide, 1H, H-3), 10.4 (s, wide, 1H, NH-5), 11.23 (s wide, 1H, NH-2).

(C)

8-hydroxy-4-methyl-2H,5H-pyrido(4,3-b)-1-indolone

A mixture of the ketone previously obtained (1.37 g) and of palladized charcoal at 10% (1 g) in diphenylether (100 ml) is heated to reflux under agitation for 30 minutes and then cooled to ambient temperature. 400 ml of ethanol is added, followed by filtering and washing the solid with 200 ml of boiling ethanol, and evaporating off the ethanol under reduced pressure. After addition of 150 ml of toluene to the residual diphenylether, the precipitate obtained is filtered off, dried and taken up in boiling dioxane containing a sufficient quantity of ethanol to dissolve it.

The filtered solution is concentrated to eliminate the ethanol and cooled to provide clear-beige crystals (1.1 g).

Yield: 81%: m.p. >260° C.

Calculated for $C_{12}H_{10}N_2O_2$: C, 67.28: H, 4.71: N, 13.08. Found: C, 66.89: H, 4.74: N, 12.84.

NMR $H_1$ [$(CD_3)_2SO$]: δ: 2.25 (s, 3H, $CH_3$-4), 6.8 (q, 1H, H-7, J 7-6=9 Hz, J 7-9=2.3 Hz), 7.07 (m, 1H, OH-8), 7.32 (d, 1H, H-6), 7.56 (d, 1H, H-9), 8.92 (s, 1H, H-3), 10.09 (s wide, 1H, NH-5), 11.4 (s wide, 1H, NH-2).

(D)

8-benzoyloxy-4-methyl-2H,5H-kpyrido(4,3-b)-1-indolone

The preceding pyrido indolone (4 g) is treated with benzoic anhydride in excess (12.6 g) in pyridine (100 ml) at reflux for 2 hours 15 minutes, then the pyridine is evaporated off. The residue is taken up in a solution of sodium acid carbonate in excess and the aqueous phase is decanted after agitation for one hour. 50 ml of ethanol is added to the insoluble fraction and the precipitate obtained is separated, washed with cold ethanol and then taken up in boiling ethanol (100 ml) for 5 minutes.

The cooled mixture provides 4.4 g of clear-beige micro-crystals.

Yield: 74%: m.p. >260° C.

Calculated for $C_{19}H_{14}N_2O_3$: C, 71.69: H, 4.43: N, 8.80. Found: C, 71.32: H, 4.39: N, 8.81.

NMR $H_1$ [$(CD_3)_2SO$]: δ: 2.31 (s, 3H, $CH_3$-4), 7.16 (s, 1H, H-3), 7.24 (q, 1H, H-7, J 7-6=8.5 Hz, J 7-9=1.8 Hz), 7.6 (d, 1H, H-6), 7.73 (m, 3H of $C_6H_5$), 7.96 (d, 1H, H-9), 8.23 (m, 2H of $C_6H_5$), 10.96 (s wide, 1H, NH-2), 11.92 (s wide, 1H, NH-5).

We claim:

1. Compounds with the formula (I)

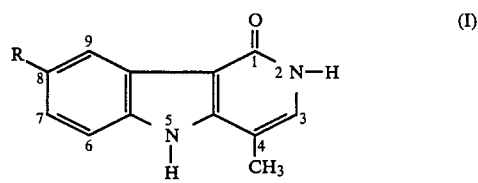

in which R represents hydrogen or a $C_1$–$C_4$ alkoxy group or a ($C_6$–$C_{10}$) aryl carbonyloxy group.

2. Process for the preparation of the compounds (I) according to claim 1, characterized in that:
  (a) 1,2-dihydro-4-hydrazino-5-methyl-2-oxo pyridine is made to react on cyclohexanone, possibly carrying a substituent in position 4 in order to obtain the hydrazone with the formula (II)

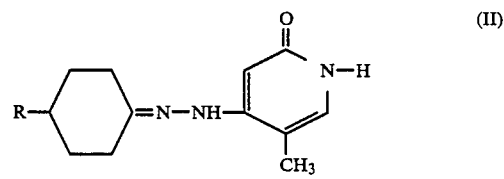

in which R has the same significance as in formula (I), (b) the hydrazone with the formula (II) is cyclized in order to obtain a 1,2,6,7,8,9-hexahydro-4-methyl-1-oxo-5H-pyrido(4,3-b)indole with the formula (III)

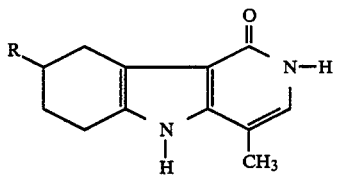

(III)

in which R has the same significance as in formula (I)

(c) the hexahydro pyrido-indole of formula (III) is dehydrogenated in order to obtain the 1,2-dihydro-4-methyl-1-oxo-5H-pyrido(4,3-b)indole of formula (I).

3. Process according to claim 2, characterized in that according to a variant, the dehydrogenation of the compound with the formula (III) is carried out without preliminary isolation.

4. Process according to claim 2, characterized in that the cyclization of the hydrazone with the formula (II) into hexahydro pyrido-indole with the formula (III) takes place in the absence of a catalyst, at a temperature between 200° and 280° C.

5. Process according to claim 2, characterized in that the dehydrogenation of the compound with the formula (III) takes place in the presence of a catalyst which is palladized charcoal, at a temperature between 200° and 280° C.

6. Process according to claim 3, characterized in that the dehydrogenation of the compound with the formula (III) takes place in the presence of a catalyst which is palladized charcoal, at a temperature between 200° and 280° C.

7. A compound according to claim 1 wherein R is benzoyloxy.

* * * * *